United States Patent [19]

White

[11] Patent Number: 5,761,540
[45] Date of Patent: *Jun. 2, 1998

[54] ILLUMINATION DEVICE WITH MICROLOUVER FOR ILLUMINATING AN OBJECT WITH CONTINUOUS DIFFUSE LIGHT

[75] Inventor: Timothy P. White, New Boston, N.H.

[73] Assignee: Northeast Robotics, Inc., Weare, N.H.

[*] Notice: The term of this patent shall not extend beyond the expiration date of Pat. No. 5,604,550.

[21] Appl. No.: 821,961

[22] Filed: Feb. 14, 1997

Related U.S. Application Data

[63] Continuation-in-part of Ser. No. 501,213, Jul. 11, 1995, Pat. No. 5,604,550, which is a continuation-in-part of Ser. No. 331,882, Oct. 31, 1994, Pat. No. 5,539,485.

[51] Int. Cl.$^6$ ................................................ G03B 15/02
[52] U.S. Cl. ............................ 396/4; 396/429; 362/16
[58] Field of Search ........................ 396/4, 429; 362/16, 362/17

[56] References Cited

U.S. PATENT DOCUMENTS

| | | |
|---|---|---|
| 2,792,740 | 5/1957 | Haynes . |
| 2,926,559 | 3/1960 | Oppenheimer . |
| 2,934,601 | 4/1960 | Oppenheimer . |
| 3,322,487 | 5/1967 | Renner . |
| 3,558,894 | 1/1971 | Odone et al. . |
| 3,596,083 | 7/1971 | Lovering . |
| 3,944,336 | 3/1976 | Carr, Jr. . |
| 3,984,157 | 10/1976 | LeVantine . |
| 3,985,425 | 10/1976 | Clapp . |
| 4,067,026 | 1/1978 | Pappanikolaou . |
| 4,139,306 | 2/1979 | Norton . |
| 4,185,902 | 1/1980 | Plaot . |
| 4,341,449 | 7/1982 | Iwata et al. . |
| 4,555,635 | 11/1985 | Yoshida . |
| 4,561,722 | 12/1985 | Smetana . |
| 4,601,576 | 7/1986 | Galbraith . |
| 4,677,473 | 6/1987 | Okamoto et al. . |
| 4,691,231 | 9/1987 | Fitzmorris et al. . |
| 4,712,889 | 12/1987 | Schindl . |
| 4,791,534 | 12/1988 | Lindberg . |
| 4,816,686 | 3/1989 | Hara et al. . |
| 4,854,688 | 8/1989 | Hayford et al. . |
| 4,877,326 | 10/1989 | Chadwick et al. . |
| 4,882,498 | 11/1989 | Cochran et al. . |
| 4,965,665 | 10/1990 | Amir . |
| 4,972,093 | 11/1990 | Cochran et al. . |
| 4,991,947 | 2/1991 | Sander et al. . |
| 5,011,265 | 4/1991 | Tamamura et al. . |
| 5,039,868 | 8/1991 | Kobayashi et al. . |
| 5,051,825 | 9/1991 | Cochran et al. . |
| 5,060,065 | 10/1991 | Wasserman . |
| 5,064,291 | 11/1991 | Reiser . |
| 5,072,127 | 12/1991 | Cochran et al. . |
| 5,104,210 | 4/1992 | Tokas ........................ 359/269 |
| 5,155,558 | 10/1992 | Tannenbaum et al. . |
| 5,172,005 | 12/1992 | Cochran et al. . |
| 5,187,611 | 2/1993 | White et al. . |
| 5,461,417 | 10/1995 | White et al. . |
| 5,539,485 | 7/1996 | White ........................ 396/429 |
| 5,604,550 | 2/1997 | White ........................ 396/429 |

Primary Examiner—David M. Gray
Attorney, Agent, or Firm—Davis and Bujold

[57] ABSTRACT

An illumination device for illuminating an object to be observed, by a machine vision camera or the like for example, with a continuous diffuse wide angle light which is supplied along the observation axis of the machine vision camera. The diffuser is mounted parallel to the observation axis but separated from the beam splitter by a microlouver filter so that the microlouver filter prevents diffused light from the diffuser from directly illuminating any point of interest on the surface of the object to be observed. The microlouver filter only allows indirect illumination of the object to be observed by the diffuser and provides improved uniform illumination of the object to be observed.

20 Claims, 9 Drawing Sheets

5,761,540

ILLUMINATION DEVICE WITH MICROLOUVER FOR ILLUMINATING AN OBJECT WITH CONTINUOUS DIFFUSE LIGHT

This is a Continuation-In-Part of application Ser. No. 08/501,213 filed Jul. 11, 1995 now U.S. Pat. No. 5,604,550 which is a Continuation-In-Part of application Ser. No. 08/331,882 filed Oct. 31, 1994, now U.S. Pat. No. 5,539,485.

FIELD OF THE INVENTION

This invention pertains to an illumination device for illuminating an object to be observed, by a machine vision camera or the like for example, with a continuous diffuse wide angle light whose illumination is supplied both along the viewing axis of the machine vision camera and off axis and includes a louver member which is positioned between a diffuser and a beam splitter which prevents light from the diffuser from directly illuminating any point of interest on the surface of the object to be observed.

BACKGROUND OF THE INVENTION

Robotics assembly machines often utilize video cameras to observe the component, part or work piece being handled, machined or assembled. For instance, in the assembly of electronic components, the chips or wafers are often assembled into printed circuit boards by robots utilizing video cameras to position the components and/or to inspect the assembled device for defects throughout the process.

In the microelectronics industry, solder pads on surface-mount devices are often observed by machine vision systems for assembly and manufacturing purposes. The accuracy and reliability of a machine vision system is critical for proper alignment of the numerous components which are to be mounted on a printed circuit board. For optimum alignment, solder pads must be clearly observed in high contrast with their background.

Components in many industries often utilize etched characters appearing on mirror like surfaces that serve to identify the components and to accurately position them during assembly. In order to permit a clear image of the characters to be produced in the camera For accurate manipulation of the parts by the robotics handling equipment, it is important that the observed object be properly illuminated.

Proper illumination of many different shiny and uneven surfaces, e.g. solder connections, foil packaging, ball bearings, etc., is critical if high quality robotics assembly is to be achieved. However, such shiny and uneven surfaces are difficult to illuminate for accurate video imaging, and this creates a need for improved illumination of such objects being observed by machine vision cameras.

When using previously available illumination systems to illuminate work pieces having uneven, highly reflective surfaces, the uneven reflection of light from these surfaces frequently produces erroneous images and signals when viewed through the camera thereby possibly resulting in an erroneous signal or incorrect/inaccurate measurement. Errors of one or two thousands of an inch in a fiducial location measurement for a single component are sufficient to ruin a large and expensive circuit board. Furthermore, previously available illumination systems for robotics handling of items have not produced a light which is uniform over the entire object being observed. As a result, the reflected image suffers from erroneous shadows, glints and glare thereby rendering it difficult to determine the precise location or quality of the object.

To date, many illumination devices have been developed to provide substantially uniform illumination of an object to be viewed, but such known illumination devices are fairly large and cumbersome and are thus difficult to integrate into an electronic manufacturing process. For example, one of the Inventor's known light system might occupy a volume of 300 cubic inches and weigh several pounds, thereby adding to the costs and expense in constructing machine vision equipment in a very competitive industry. It is desirable to manufacture a miniature illumination device which may occupy 8 cubic inches or less and only weigh a few ounces. Such miniaturization allows significant cost savings and lessens the expense of the machinery for inspecting manufactured products.

The term "diffuse", as used in this specification and appended claims, means a light source which is uniformly dispersed over a broad range of incident angle of azimuth and elevation with respect to the object being observed, and the light source approaches complete coverage over the area where the light is directed, i.e. greater than 80% of the possible angular range of incident light-approaching area X in FIG. 12. The term "concealed" as used in this specification and appended claims, when referring to the diffuser and the object to be observed, means that the surface emitting the diffused light from the diffuser is positioned such that the emitting surface of the diffuser can not directly illuminate the object, i.e. only indirect illumination of the object by reflection of light off the beam splitter or the side wall(s) of the housing or supplying light through the beam splitter can occur.

SUMMARY OF THE INVENTION

Wherefore it is an object of the invention to overcome the above noted drawbacks of the prior art illumination devices.

It is another object of the present invention to develop an improved continuous diffuse illumination device for machine vision systems having a simplistic design which precisely determines the location of the object being observed.

It is a further object of the invention to develop an improved diffuse wide angle illumination field to improve image quality and uniformity of appearance of uneven specular surfaces, such as those found in the electronic and pharmaceutical manufacturing processes, e.g. circuit boards, components, pills, capsules, and their packaging.

A still further object of the invention is to provide an adaptor for an existing diffuse illumination device that increases the uniformity of the illumination provided thereby and achieves a substantially symmetrical illumination geometry.

Yet another object of the invention is to increase (e.g. double) the brightness of the light reflected by the beam splitter to make such reflected light appear more equal in brightness to the light reflected by the diffusely reflecting inner surfaces of the surrounding housing structure.

A further another object of the invention is to minimize the brightness of the direct light from the diffuser to the object to the same range of brightness as the light reflected by the beam splitter and the surrounding housing structure.

Still another object of the invention is to minimize uneven illumination of the object to be observed and the area adjacent the object, e.g. maximize the range of elevational angles of incident which commonly occur with simple beam-splitter illumination devices (e.g. Carr et al. (U.S. Pat. No. 3,944,336) for example) where the beam splitter is planar and its bottom edge is substantially flush with the bottom aperture of the housing.

Another object of the invention is to space the diffuser a sufficient distance from the opening so that, in use, the diffuser is completely invisible to the object being observed whereby direct illumination of the diffuser of the object by the diffuser is prevented by the housing for the diffuser.

A further object of the invention is to simplify the design of the diffuser and thereby reduce the amount of material required to manufacture the diffuser as well as the time, cost and production in machining and/or forming an necessary angle required of the diffuser.

A still further object of the invention is to minimize or eliminate any direct illumination of the object being observed by the diffuser to facilitate even illuminate of the object being imaged.

Yet another object of the invention is to provide a filter, located between the beam splitter and the diffuser, which prevents direct illumination by the diffuser of the object to be observed.

Still another object of the invention is to provide a filter, located between the beam splitter and the diffuser, which prevents direct illumination by the diffuser of the object to be observed.

These and other objects of the invention are realized by an illumination device for illuminating an object to be observed by a camera along an observation axis extending from the camera to the object, said illumination device comprising: a housing having at least a first aperture therein alignable with an observation axis; a partially reflective beam splitter being supported by said housing and being positioned obliquely relative to the observation axis adjacent said at least first aperture; a light source being arranged to cast light on a first surface of said beam splitter; a diffuser being positioned between said beam splitter and said light source for diffusing light from said light source as the light passes through said diffuser to said first surface of said beam splitter; and a louver filter being positioned between said beam splitter and said diffuser to prevent direct illumination an object to be observed whereby said diffuser is only able, during use, to indirectly illuminate a desired portion of the object to be observed, via said louver filter and said beam splitter, when the object is positioned along the observation axis.

The invention also relates to an inspection system for illuminating an object to be observed by a camera along an observation axis extending from the camera to the object, said inspection system including an illumination device in combination with a camera, said illumination device comprising: a housing having at least a first aperture therein aligned with an observation axis; a partially reflective beam splitter being supported by said housing and being positioned obliquely relative to the observation axis adjacent said at least first aperture; a light source being arranged to cast light on a first surface of said beam splitter; a diffuser being positioned between said beam splitter and said light source for diffusing light from said light source as the light passes through said diffuser to said first surface of said beam splitter; and a louver filter being positioned between said beam splitter and said diffuser to prevent direct illumination an object to be observed whereby said diffuser is only able, during use, to indirectly illuminate a desired portion of the object to be observed, via said louver filter and said beam splitter, when the object is positioned along the observation axis defined by the camera thereby facilitating determination by the camera of one of a desired feature and characteristic of the object to be observed.

The invention also relates to a method of illuminating an object to be observed by a camera along an observation axis extending from the camera to the object, said method comprising the steps of: utilizing a housing having two aligned apertures therein which are both aligned with an observation axis; supporting a partially reflective beam splitter within said housing between said apertures and along the observation axis; arranging a light source to cast light on a first surface of said beam splitter; positioning a diffuser between said beam splitter and said light source for diffusing light from said light source as the light passes through said diffuser toward said beam splitter; positioning a louver filter between said beam splitter and said diffuser to prevent direct illumination an object to be observed by said diffuser; supply light, from said light source, through said diffuser and said louver filter; reflecting a portion of said light, via said beam splitter, toward the object to be observed; allowing a portion of light reflected back by said object to be observed to pass through said beam splitter and be sensed by said camera whereby said diffuser is only able, during use, to indirectly illuminate a desired portion of the object to be observed when the object is positioned along the observation axis.

BRIEF DESCRIPTION OF THE DRAWINGS

The invention will now be described, by way of example, with reference to the attached drawings, in which.

DESCRIPTION OF THE PREFERRED EMBODIMENTS

Figure 2:
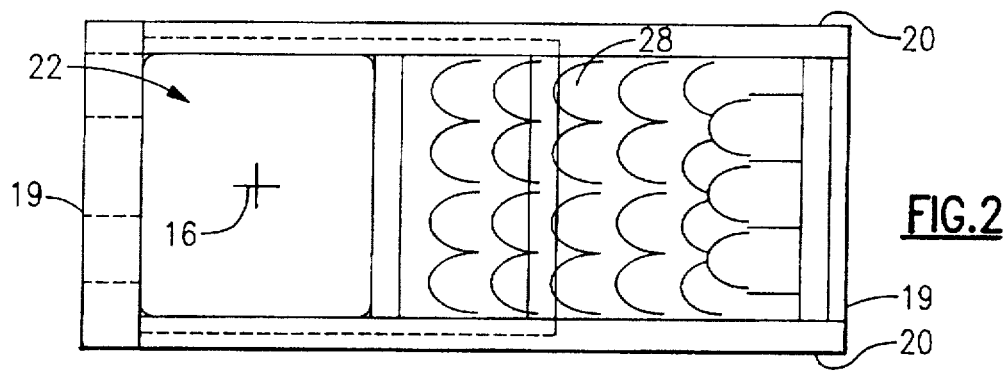
FIG. 2 is a diagrammatic top plan illustration of the continuous diffuse illumination device of FIG. 1 prior to installation of the inspection camera and other associated assembly equipment.

Turning now to FIGS. 1–4, the first embodiment of the invention will now be described in detail.

As shown in FIGS. 1–4, a housing 18 encases the various components of the continuous diffuse illumination device 2. The housing 18 comprises a first pair of spaced apart parallel side walls 19, a second pair of spaced apart parallel side walls 20 and a roof wall 21 and a base wall 21'. An aperture 22 is formed in both the roof wall 21 and the base wall 21' and the apertures 22 are concentric with one another and located along the observation axis 16. The housing accommodates therein at least one light source 28 adjacent one of the side walls 19, a beam splitter 23 is located remote from the light source 28 and positioned along the observation axis, a light diffuser, shown generally as 24, is located between the light source 28 and the beam splitter 23, and a light trap 26 is supported by the side wall 19 opposite the side wall 19 adjacent the light source 28. The arrangement of these components is such that the light source 28 casts light upon the diffuser 24 which, in turns, diffuses the light from the light source 28 and casts the diffused light upon the beam splitter 23 which reflects a desired portion of the diffused light toward the object 12. Any unreflected light which passes through the beam splitter 23 is absorbed by the light trap 26 located adjacent the beam splitter 23.

The beam splitter 23 has a partially reflective first surface 27. A desired portion of the light, e.g. approximately half of the light, from the diffuser 24 impacting upon the reflective first surface 27 of the beam splitter 23 is reflected toward the object 12, while the remainder of the light passes through the beam splitter 23 and is absorbed by the light trap 26. Likewise, a portion of the light reflected back by the object 12 is transmitted toward and through the beam splitter 23 along the observation axis 16 for viewing by the camera 10. The light returned to the camera 10 is used to determine the precise shape, orientation, and/or other characteristics of the object 12. It is well known in this art how to use of the light returned to the camera 10 to determine the shape and orientation of the object 12, and thus a detail description concerning the same is not provided herein.

An important aspect of the present invention is that at least a first diffuser portion 25A is inclined with respect to the observation axis 16. In all prior art known devices of which the inventor is aware, the diffuser 24 is aligned substantially parallel to the observation axis and thus provides direct lighting of the object 12 to be observed. The first diffuser portion 25A, according to the present invention, is inclined relative to the observation axis, e.g. between an angle of about 5° and 45° and preferably approximately 25° to 40° with respect to the observation axis, so that light diffused by the first diffuser portion 25A cannot directly illuminate the object. Accordingly, light from the first diffuser portion 25A is reflected off either the inner roof wall 21 of the housing 18 or the beam splitter 23 and thus indirectly illuminates the object 12 to be observed. The inner surface of the roof wall 21 as well as the inner surface of the side walls 20 of the housing 18 can be painted with a white, gray, or another desired color or shade of paint or some other diffusely reflective substance so as to provide desired efficiency of reflection of the light diffused by the diffuser 24 onto the object to be observed to match the light reflected by the diffuser 24.

Accordingly, the first diffuser portion 25A is concealed and is not directly visible by the object 12 to be observed, i.e. the first diffuser portion 25A is inclined such that it lies along a plane indicated dashed line 38 which is to the left of the object 12 to be observed and thus can not directly illuminate the object. The second diffuser portion 25B extends vertically down from a second edge of the first diffuser portion such that a portion of the light passing through by that portion directly illuminates the object 12 and a remaining portion of the diffused light is reflected by the inner surface of the side walls 19, 20 toward the object 12.

In this manner, a portion of the light diffused by the diffuser 24 directly illuminates the object 12 over a first range of incidence angles and another portion of the light from the diffuser is reflected by the reflective second surface 27 of the beam splitter illuminating the object 12 over a second range of incidence angles.

Figure 9:
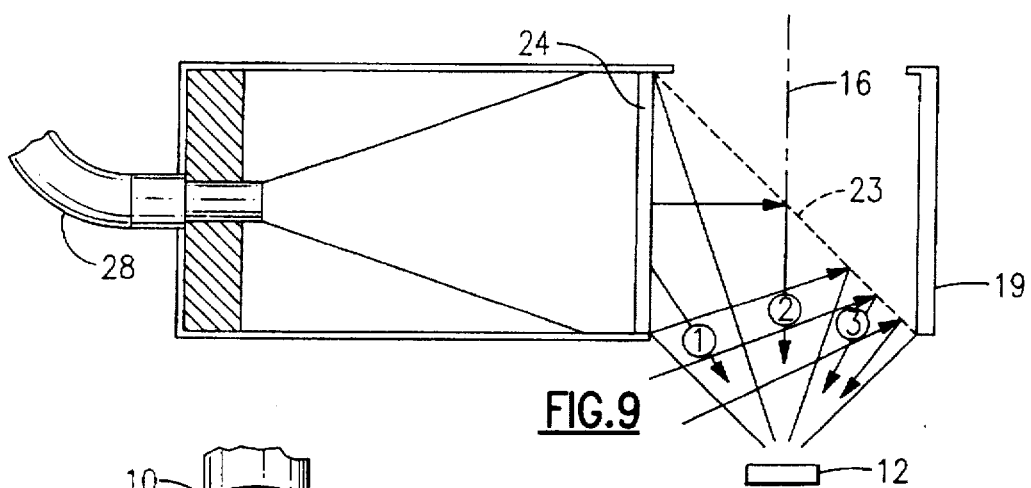
FIG. 9 is a diagrammatic plan view of a prior art illumination device showing the area which is poorly and/or non-uniformly illuminated.

In order to cause light to be reflected to the object 12 from the entire surface of the beam splitter 23, rather than being limited to an area of the beam splitter surface bounded on its lower side by a point reflecting a ray of light from the bottom edge of the diffuser 24 to the object 12, as generally occurs with known illumination devices, making use of beam splitter reflecting diffuse light sources adjacent to the observation axis, the present invention increases the length of the side walls 19, 20 so that the spacing of the roof wall 21 from the base wall 21' is increased, e.g. substantially doubled, over the proportional spacing of the roof and base walls of the known illumination devices. The extended side walls, according to the present invention, provide greater housing surface area for reflecting the light passing through the diffuser 24 and results in a substantially greater range of angle of incident uniform lighting of the object 12 to be observed (FIG. 9).

Figure 1:
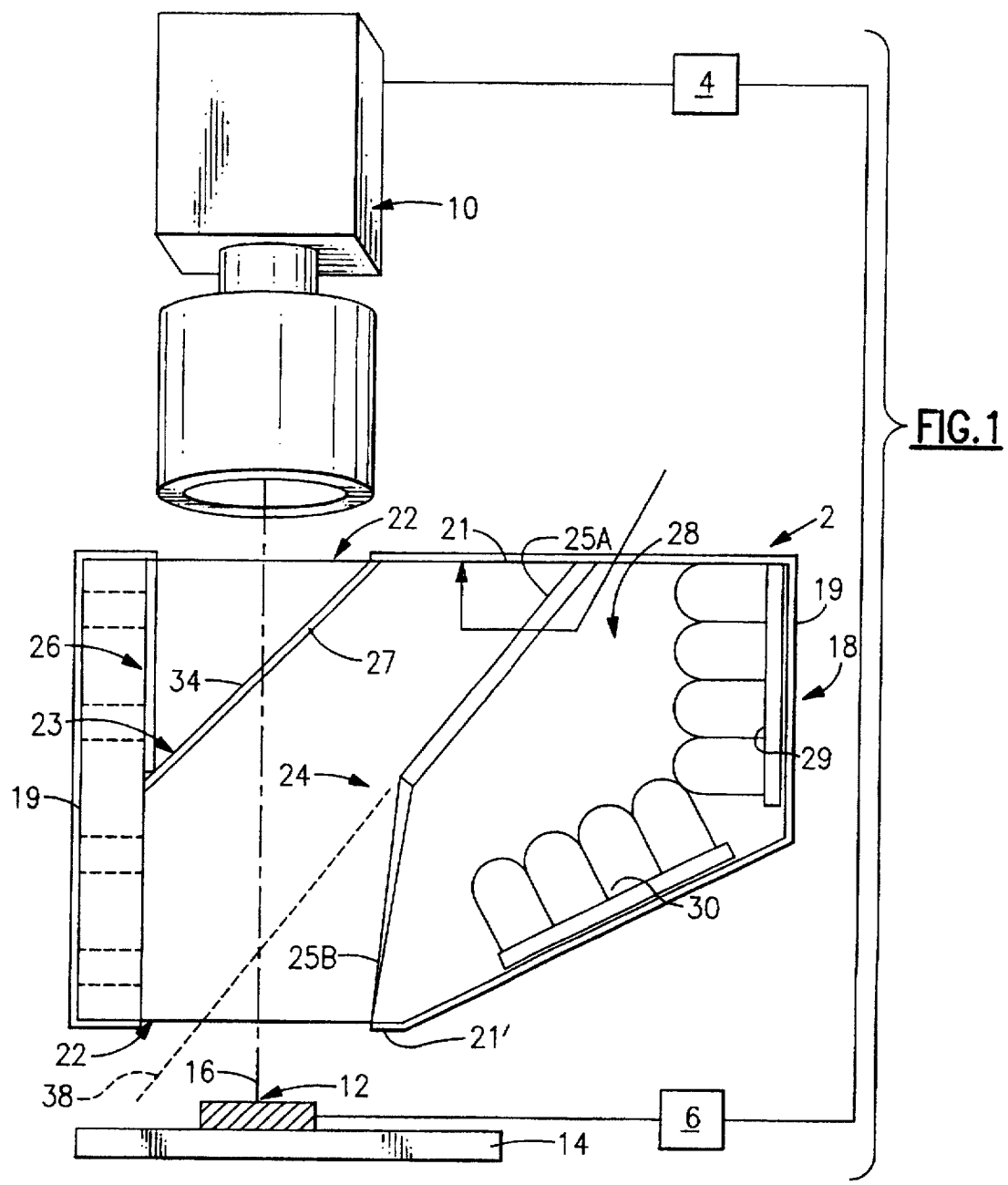
FIG. 1 is a diagrammatic illustration of an improved continuous diffuse illumination device, equipped with an inspection camera and other associated assembly equipment, providing light both along the observation axis and at an angle to the observation axis according to the present invention.
Figure 3:
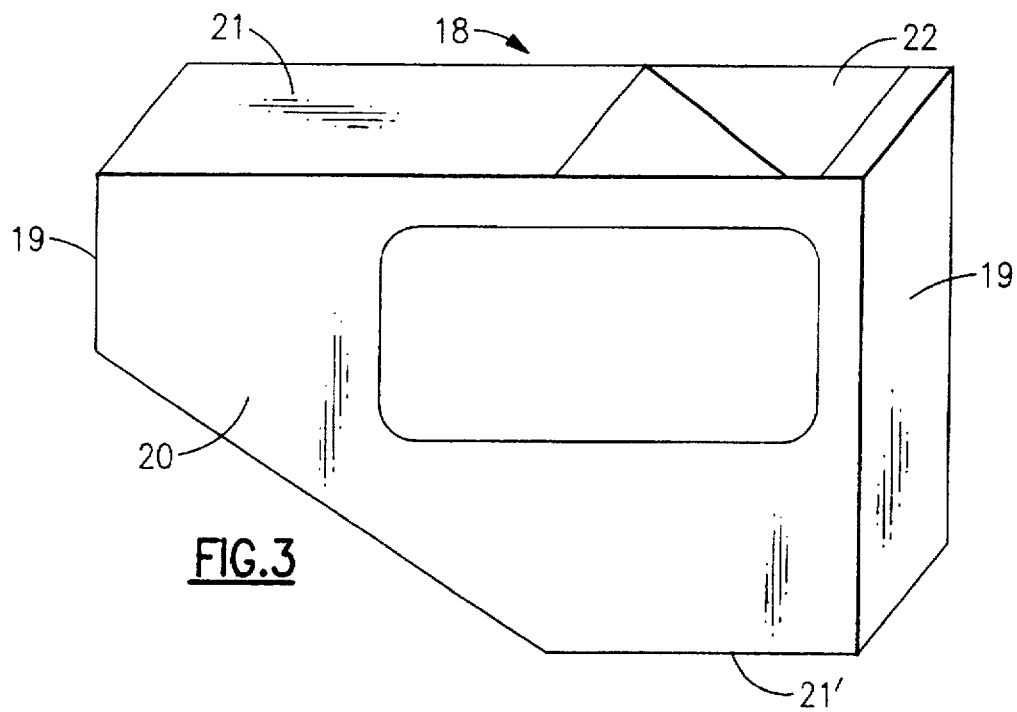
FIG. 3 is a diagrammatic perspective illustration of FIG. 1 prior to installation of the inspection camera and other associated assembly equipment.
Figure 4:
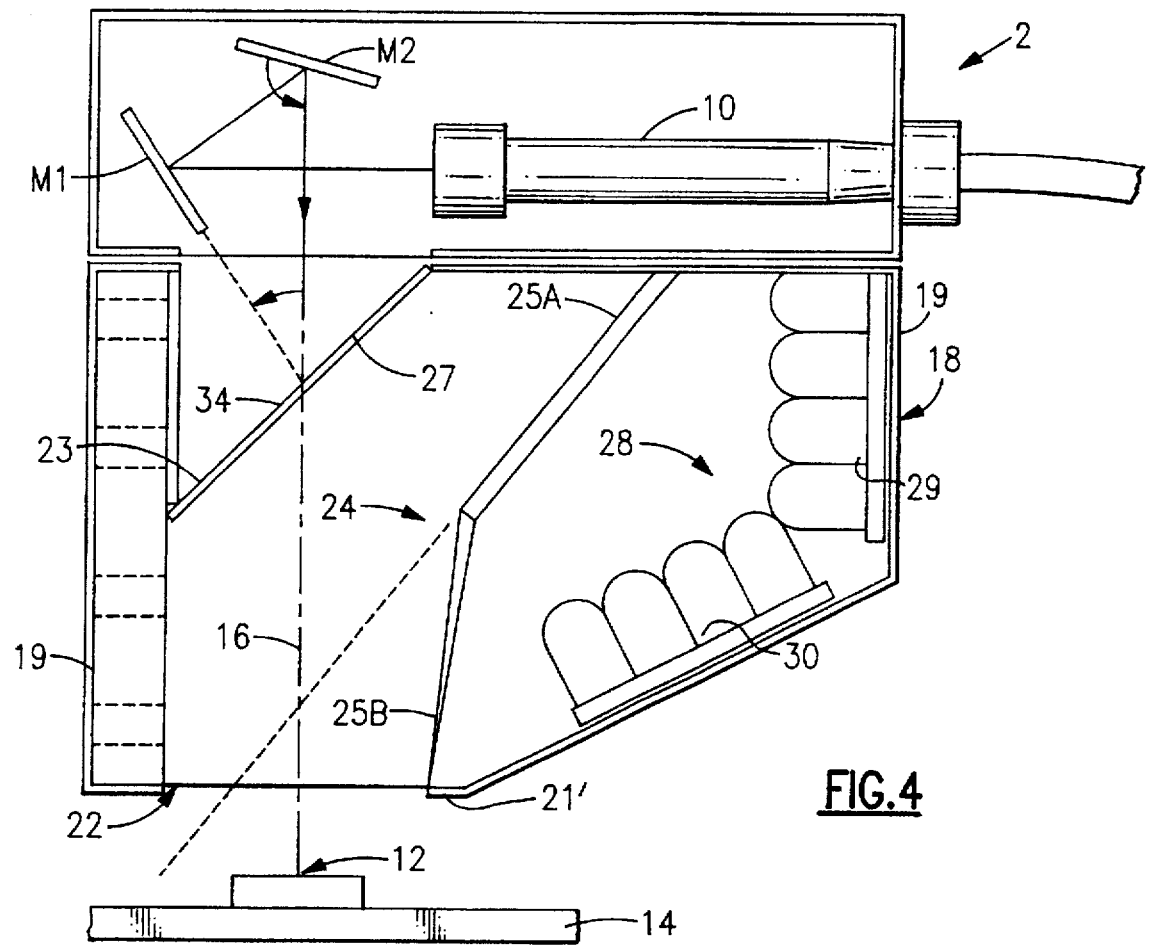
FIG. 4 is a diagrammatic illustration, similar to that of FIG. 1, showing a second embodiment of the attachment of the inspection camera.
Figure 6:
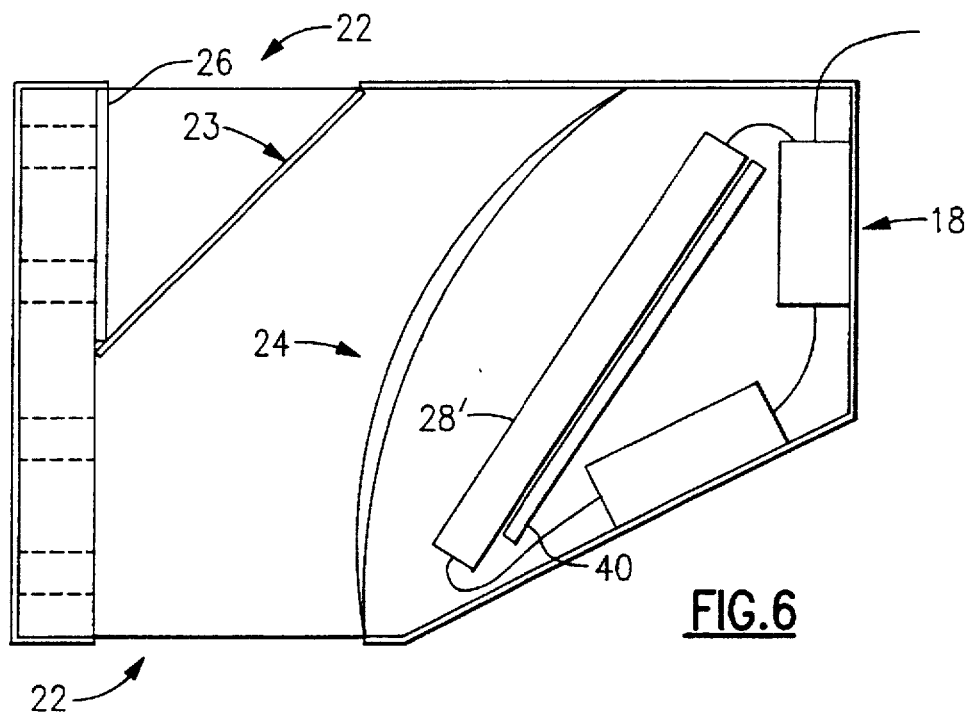
FIG. 6 is a diagrammatic illustration of a third embodiment of an improved continuous diffuse illumination device, providing light both along the observation axis and at an angle to the observation axis, according to the present invention.

Second diffuser portion 25B is made of a translucent diffusing material selected of a material and thickness profile to pass approximately as much light directly to the object 12 as is reflected to the object 12 from the beam splitter 23 (see FIGS. 1, 4 and 6).

Figure 5:
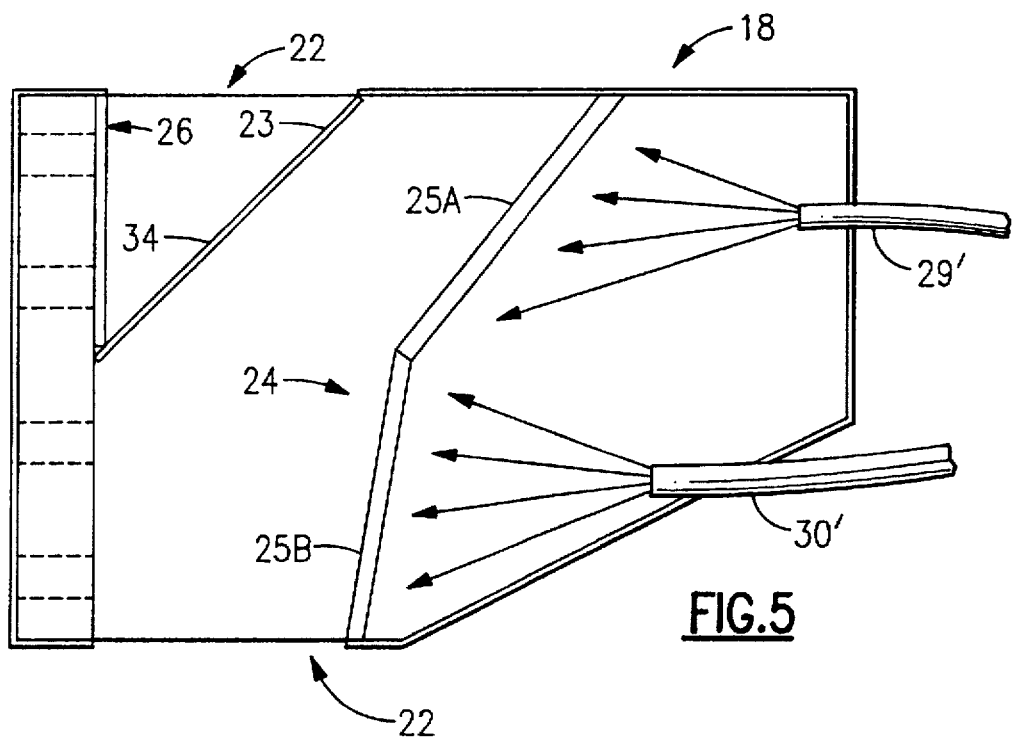
FIG. 5 is a diagrammatic illustration of a second embodiment of an improved continuous diffuse illumination device, providing light both along the observation axis and at an angle to the observation axis, according to the present invention.

The light source 28 is either a single source of light (FIG. 6) in the form of first 29 and second 30 light arrays (FIGS. 1 and 4) or is first and second light members 29', 30' (FIG. 5). The diffuser 24 can likewise either be a single diffuser member, e.g. a curved member having a radius of curvature approximately four times the aperture width 22 for example, in which the curvature is designed to approximate the first and second diffuser portions of the diffuser. Alternatively, the diffuser 24 is in the form of first and second diffuser portions 25A, 25B, e.g. first and second planar diffuser members. The entire inner surface of the housing 18, including the inner surface to the right of the diffuser 24 in FIGS. 1 and 4, is preferably coated with a substance, e.g. paint, which promotes directed reflection of the light generated by the first and second light arrays 29, 30 and reflection of the light diffused by the diffuser.

The present invention is also directed at increasing the apparent brightness of the beam splitter so that the portion of the light which is reflected, toward the object 12 to be observed, by the beam splitter 23 closely matches the brightness of the light reflected by the inner surfaces of the housing 18 whereby a more uniform field of illumination is supplied to the object 12 and an improved viewing of the object 12 by the camera 10 is achieved. There are a number of ways in which the brightness equalization can be accomplished. If a single light source is used to illuminate both the first and second diffuser portions, then the first diffuser portion 25A can be machined or modified to allow twice as much light to pass therethrough than the second diffuser portion 25B. Alternatively! if two light sources are utilized, the intensity of the light source associated with the first diffuser portion 25A (see FIG. 5) can be accordingly increased by a light intensity controller 25C or two or more light sources may be associated with the first diffuser portion 25A and such two or more light sources light sources may be positioned at different angles.

FIG. 4 shows a second arrangement for mounting the camera to the illumination device 2. In this embodiment, the camera 10 is a micro television camera with a lens and the longitudinal axis of the camera 10 extends substantially perpendicular to the observation axis 16. The camera 10 is provided with a pair of mirrors M1 and M2 for reflecting the light returned along the observation axis 16. For example, here mirrors Ml and M2 are oriented at angles selected to cause the camera's optical axis and the observation axis to substantially coincide. In this figure, the mirror M1 is oriented at an angle of 64.5° with respect to the observation axis 16 while the mirror M2 is oriented at angle of 112.5° with respect to the observation axis 16 thereby resulting in a perpendicular reflection.

The embodiment of FIG. 5 is similar to the previous embodiment except that the light arrays 29 and 30 are replaced with a pair of fiber optic light guides 29' and 30'. Each one of the fiber optic guides 29' and 30' is directed to shine light on a desired one of the first and second diffuser portions. It is to be appreciated that the number and orientation of the light sources, the light arrays, the fiber optic guide, etc., can be varied depending upon the application at hand.

FIG. 6 is a further embodiment of the present invention in which both the diffuser and the light source have been modified. In this embodiment, the diffuser 24 is a curved non-planar member. In addition, the two light arrays 29 and 30 are replaced with a single light source 28' which is a miniature fluorescent light array, electro luminescent panel or fiber optic diffuser, for example. The miniature fluorescent light array is powered by a pair of conventional power supplies, with or without separate illumination intensity controllers (not numbered), and, as such teaching is well known in the art, a further description concerning such light is not provided herein. A rear surface of the miniature fluorescent light array 28' is provided with a planar reflector member 40 which reflects the fluorescent light, directed toward the reflector member 40, back toward the diffuser 24. The diffuser 24 is preferably tapered at least at one end, preferably at both ends, depending on the application, to equalize the amount of the light that will pass through the diffuser 24. Typically, when a fluorescent light is used, the generated light is brighter in the central region of the fluorescent light and dimmer at the end regions. The taper of the diffuser at both ends allows the light to pass more readily through the diffuser and thereby compensate for the lower amount of light available in the end regions of the diffuser 24.

Figure 7:
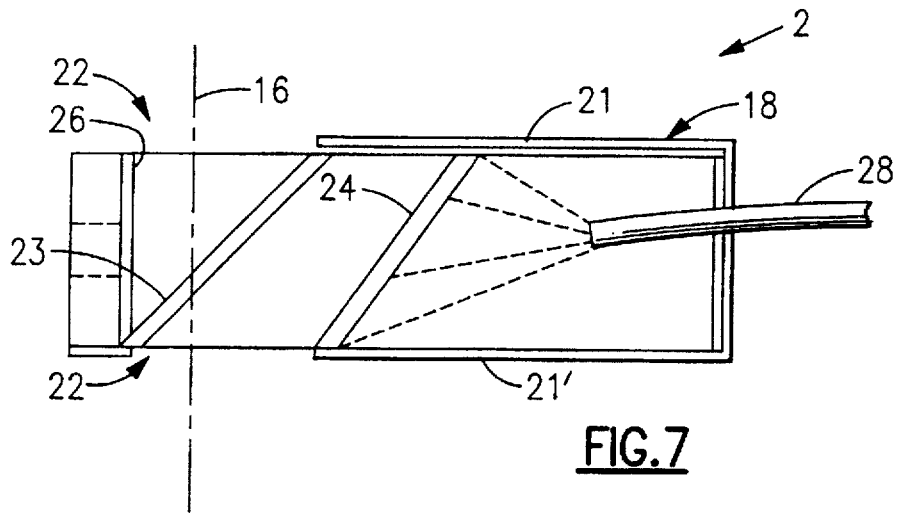
FIG. 7 is a diagrammatic illustration of a fourth embodiment of the present invention.

Turning now to FIG. 7, only a single planar diffuser member is utilized and accommodated within the housing 18. The diffuser is tilted at an angle of approximately 25°–40° with respect to the observation axis 16 so as not to be visible by the object 12, i.e. "concealed", when positioned for observation. In addition, only a single light source 28 is employed. However, due to the tilting of the diffuser 24, the diffuser cannot directly illuminate the object 12 to be observed unless the object is placed substantially in the aperture 22 provided in the base wall 21' of the housing 18. Accordingly, the object 12 is not directly illuminated, i.e. is "concealed", but receives a desired amount of incident light reflected by the inner surfaces of the side walls and inner roof wall of the housing and thereby results in a more uniform lighting of the object 12 than prior art illumination devices.

Figure 8:
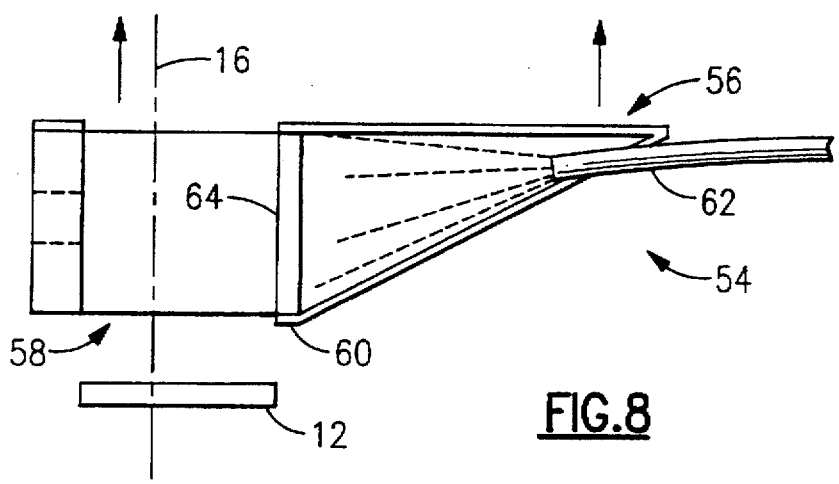
FIG. 8 is a diagrammatic illustration showing an adaptor for the fourth embodiment of FIG. 7 to provide all the advantages of one embodiment of the present invention.

An adaptor to be utilized in combination with the illumination device 2 of FIG. 7 will now be described with reference to FIG. 8. The adaptor 54 comprises a housing 56 having an aperture 58 in the end wall 60 thereof. A roof wall is not necessary and thus the top of the adaptor may be open. The housing 56 contains a light source 62 and a second diffuser 64. The diffuser may extend substantially parallel to the observation axis 16 or may be inclined a small angle relative to that axis, e.g. a few degrees. The adaptor 54 is connected to the base wall 21' of the illumination device 2, as shown by the arrows in FIG. 8. The two components 2 and 54 are securable to one another by any known securing mechanism, e.g. glue, clamps, fasteners, etc., such that the apertures 22, 58 of the two components 2, 54 are aligned along the observation axis 16. The two secured components 2, 54 together function substantially identical to the previous embodiments described above. The preferred division between the first and the second components is shown in FIGS. 7 and 8 and these two components may be sold together or independently of one another.

The beam splitter 23 is preferably in the form of a mirror beam splitter that is well known in the art, but it also could comprise a cube or a membrane. The second surface 34 of the beam splitter 23 (FIG. 1), facing the camera 10, has an anti-reflection coating disposed thereon to prevent stray light from being reflected toward the camera 10 and thereby create a false image. Preferably, magnesium chloride (MgCl) is used as the anti-reflection coating for the beam splitter 23. It is to be appreciated that any other suitable anti-reflection coating, that permits the camera 10 to observe the object 12 through the beam splitter 23 free of a double image or a ghost image, may be utilized on the second surface 34 of the beam splitter 23.

The diffuser 24 may consist of a pair of planar plate members formed of glass or plastic, as shown in FIGS. 1 and 4, each lying in a different plane and having a surface which is translucent and capable of diffusing light passing through the diffuser. The diffuser 24 may alternatively be formed of an etched or ground glass, or may be formed of opal glass having light scattering centers of colloidal particles. Frosted glass, milky plastic or a Murata screen may also be used. Murata screen is formed of a diffusing synthetic plastic material.

It is important that the diffuser 24 have wide-angle diffuser characteristics so that light cast thereon is evenly diffused by the diffuser so that a substantially uniform intensity of light passes through the diffuser for reflection toward the object 12 by the beam splitter 23.

A variety of different light sources may be used as the light arrays 28 and 29. For example, the light arrays 28 and 29 may be a rectangular configuration having a plurality of bulbs evenly spaced thereon. Alternatively, the light arrays may be incandescent fiber optics, LEDs or fluorescent lights 5. The important requirement of the light source is that it be capable of supplying a substantially uniform intensity of light to the diffuser 24 so that the diffuser 24 may evenly diffuse the light received from the light source 28 and uniformly illuminate the object 12 both along the observation axis and at an angle to the observation axis.

Preferably, the beam splitter 23 is disposed at an angle of 45° with respect to the observation axis 16, however, it will be appreciated that the angle of the beam splitter may be varied, as desired, from a 45° orientation and still function in the desired manner. If the beam splitter 23 is located at a 45° orientation with respect to the observation axis 16, it is necessary to approximately double the length of the side walls 19 and 20 to achieve substantially uniform illumination of the object 12. If the orientation is varied from 45° orientation, the length of the side walls 19 and 20 would be accordingly varied in order to provide uniform lighting of the desired object 12. The length of the side walls is determined such that the continuity of incident light, which falls on the object, is substantially uniform. In addition, the size, shape and orientation of the object 12 to be observed must be taken into account, along with the tilt angle of the first diffuser portion with respect to the observation axis, when determining the length to the side walls.

Figure 11:
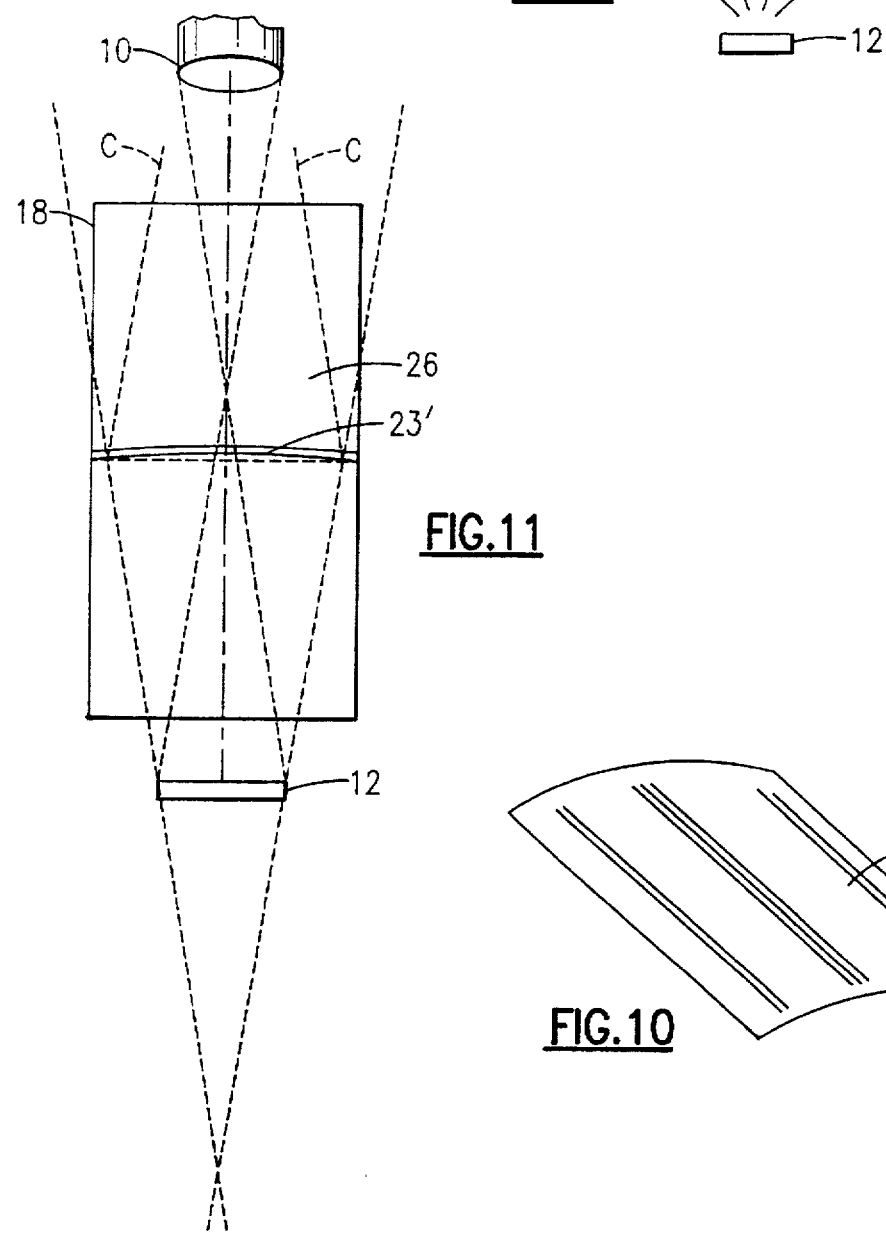
FIG. 11 is a diagrammatic end-view cross-sectional illustration of the object and camera using the curved beam splitter of FIG. 10 and showing its optical effect.
Figure 10:
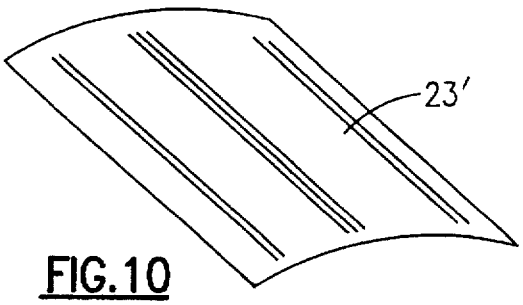
FIG. 10 is a perspective illustration of a curved beam splitter according to the present invention.

For maximum uniformity of illumination, the beam splitter 23' should be curved sufficiently (FIGS. 10 and 11) to eliminate the beam splitter 23' from reflecting light, diffused by the first diffuser portion 25A and reflected off the side walls located between the beam splitter 23' and the first diffuser portion 25A, toward the object 12 being observed, i.e. the beam splitter 23' only reflects light directed toward the beam splitter and does not reflect any light reflecting off the adjacent side walls 20, 21, 21'. In the case of an illumination device 2 having a 2 inch square aperture and a beam splitter inclined at an angle of 45° with respect to the object, the calculated radius of curvature required is 11.482 inches, which is just sufficient to cause diverging rays to be collimated from the beam splitter 23' back to the diffuser for a 2 inch square aperture. The required curvature is a function of camera 10 and the part 12 distance, however the true scale dimensions shown in FIG. 11 represent a good approximation of a typical case. As a rule of thumb, then, the radius of curvature of the beam splitter 23 should be slightly less than 11.242/2=5.621 or, to be safe, a radius of about 5.5 times the aperture dimension. This can achieved with a flexible beam splitter by making the width of the beam splitter be between 101% and 102% of its nominal flat width, and then fitting the oversize beam splitter within its original nominal width holding fixture, thereby flexing the beam splitter to the desired partially cylindrical curvature.

Figure 13:
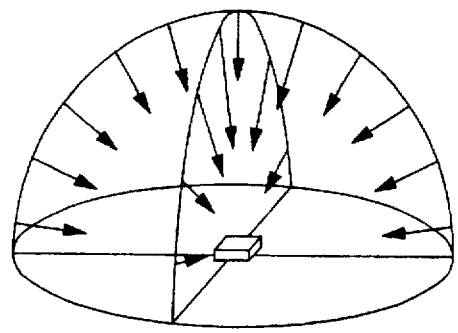
FIG. 13 is a graph of desired hemispheric lighting envelope.
Figure 12:
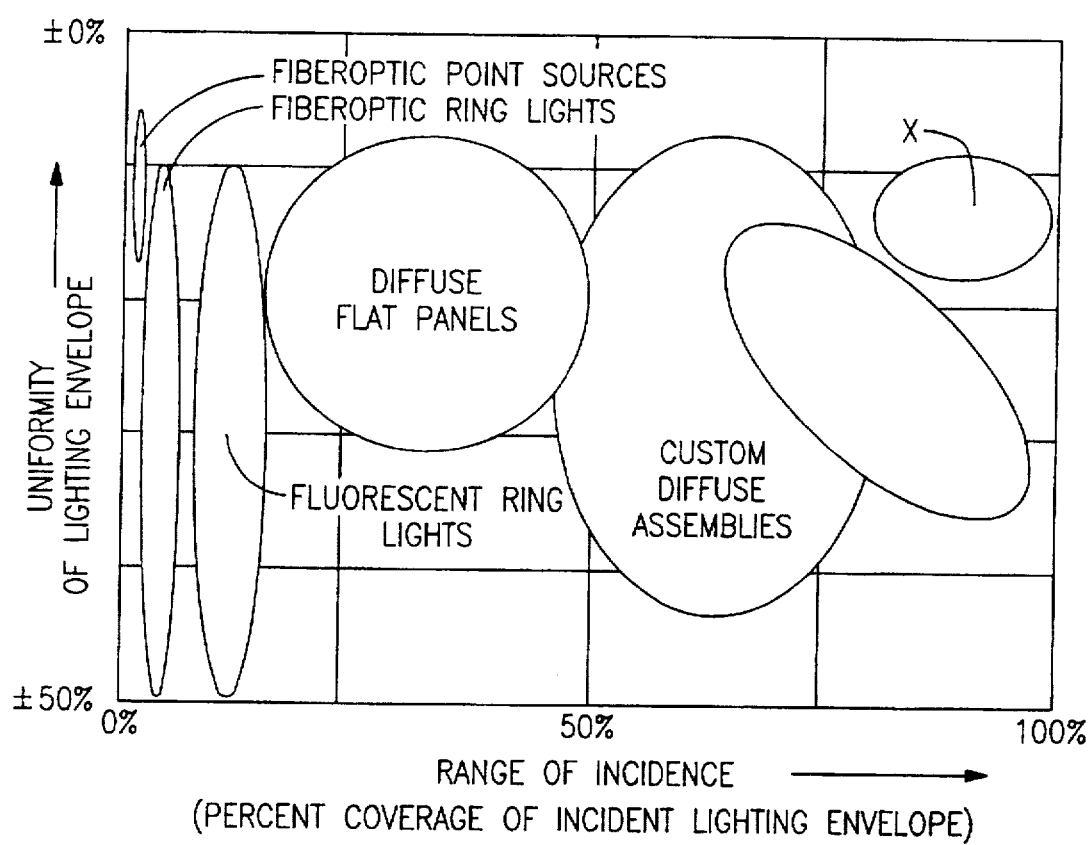
FIG. 12 is a graph depicting the characteristics of a "diffuse" light.

FIG. 12 is a graph depicting the characteristics of a diffuse light source while FIG. 13 depicts a lighting envelope which has uniformity in a complete range of incidents of the lightening envelope which is particularly adapted to determine the appearance of specular (shiny) objects and surfaces. Variations of the appearance of the specular objects and surfaces are minimized by having a continuous unbroken field of illumination and a maximum uniformity of the incident light.

The light trap 26 may consist of a planar panel defining a straight wall parallel to the observation axis 16. The light trap 26 is preferably of a flat black color so as to be capable of maximum light absorption. Alternative, a portion of the inner surface of the side wall 19 may be painted black, for example, to function as the light trap. By locating the light trap in alignment with the diffuser 24 and the beam splitter 23, light from the diffuser 24 passing through or reflected by the beam splitter 23 will be absorbed by the light trap 26 and not be reflected or supplied to the camera 10 where it could produce an erroneous signal.

A portion of the light diffused by the diffuser 24 will be reflected by the beam splitter surface 27 in a uniform manner upon the object 12. This uniform illumination of the object 12, in a symmetrical relationship of light supplied along the observation axis 16, permits the camera 10 to produce a highly accurate and unambiguous image of the object 12 free of spurious glints and shadows thereby to precisely view and determine the exact location, orientation and other visual qualities of the object being observed, particularly for shiny and uneven surfaces. This facilitates accurate robotics control of the positioning and manipulation of the object 12.

An important advantage achieved by the illumination device according to the present invention, is that a substantially uniform and diffuse lighting of the object 12 to be observed is achieved. This is accomplished, in part, by adjusting the brightness of the light supplied along the observation axis, diffused by the diffuser 24 and reflected by or supplied by the beam splitter 23, to be substantially equal in brightness to the light which is reflected by the inner surfaces of the housing side walls.

Figure 14:
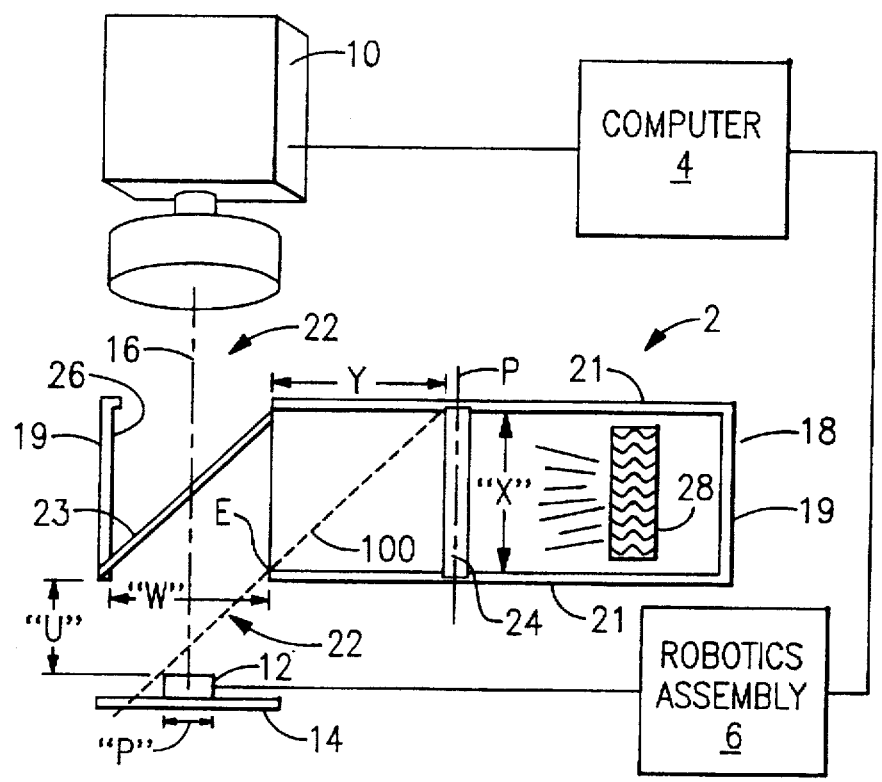
FIG. 14 is a diagrammatic illustration of a further embodiment of an improved continuous diffuse illumination device, equipped with an inspection camera, in which the entire diffuser is "concealed" from the object being observed.

Turning now to FIG. 14, an improved continuous diffuse illumination device 2 having a rectangular housing 18, a light source 28, providing light along the observation axis a light trap 26 and a beam splitter 23 is generally shown. The illumination device 2 s also equipped with an inspection device 10, i.e. a camera, a support table 14, a computer 4 and a robotics assembly or other manufacturing apparatus 6. If desired, light provided off axis may also be employed. As such components are similar or identical to the previously discussed components of the invention, a further detail discussion concerning the same is not again provide.

As with the previous embodiments, the housing 18 comprises a first pair of spaced apart parallel side walls 19, a second pair of spaced apart parallel side walls (not shown) and a roof wall 21 and a base wall 21' An aperture 22 is formed in both the roof wall 21 and the base wall 21' and the apertures 22 are concentric with one another and located along the observation axis 16. The housing accommodates therein the light source 28 adjacent one of the side walls 19, the beam splitter 23 is located remote from the light source 28 and positioned obliquely relative to and along the observation axis, the light diffuser 24 is located between the light source 28 and the beam splitter 23, and a light trap 26 is supported by the side wall 19 opposite the side wall 19 adjacent the light source 28. The arrangement of these components is such that the light source 28 casts light upon the diffuser 24 which, in turns, diffuses the light from the light source 28 and casts the diffused light upon the beam splitter 23 which reflects a desired portion of the diffused light toward the object 12. Any unreflected light which passes through the beam splitter 23 is absorbed by the light trap 26 located adjacent the beam splitter 23.

According to this embodiment, a diffuser 24 defines a plane P which extends parallel to but is spaced from, i.e. does not intersect with, the observation axis 16, i.e. at least the observation axis defined between the inspection device 10 and the beam splitter 23. That is, the diffuser 24 is recessed within the housing, i.e. spaced from the aperture 22 of the housing 18, a desired distance so as to prevent any ray of light emitted by the surface of the diffuser 24 facing the beam splitter 23 when illuminated by the light source 28, from directly illuminating any desired portion of the object 12 to be observed. A line of sight 100 between a remote portion of the object 12 to be observed and a remote portion of the diffuser 24 is such that the entire diffuser 24 is completely concealed or invisible from the desired portion of the object 12 to be observed thereby preventing direct illumination of the object 12 to be observed. It is important to note that the object 12 to be observed must be spaced from the aperture 22 a sufficient distance so that the object to be observed 12 is to the right (as seen in FIG. 14) of the line of sight 100. If the object 12 to be observed is fairly large, this means that the object 12 must be spaced further from the aperture 22 and this, in turn, may mean the illumination device parameters must be increased so as to sufficiently evenly illuminate the entire surface of the object 12 to be observed In order to achieve concealment of the diffuser in a typical application, the diffuser 24 is mounted within the housing at least 0.5 inches from an adjacent edge E of the aperture 22, and preferably spaced between about 0.5 inches and 8 inches from the adjacent edge E of the aperture 22.

When designing an illumination device according to this embodiment of the present invention, generally the following distance are taken into consideration: the distance that the object 12 to be observed is spaced from the aperture 22 (distance U) the overall size (width) of the desired portion of the object 12 to be observed (distance P), the size of the aperture 22 (distance W), the overall height dimension of the diffuser 24 (distance X), and the distance that the diffuser 24 is spaced from the aperture 22 (distance Y). Generally, it is desirable to place the object 12 to be observed fairly close, e.g. within a few inches or so, to the aperture 22 to minimize the area required to be uniform illuminated.

Figure 16:
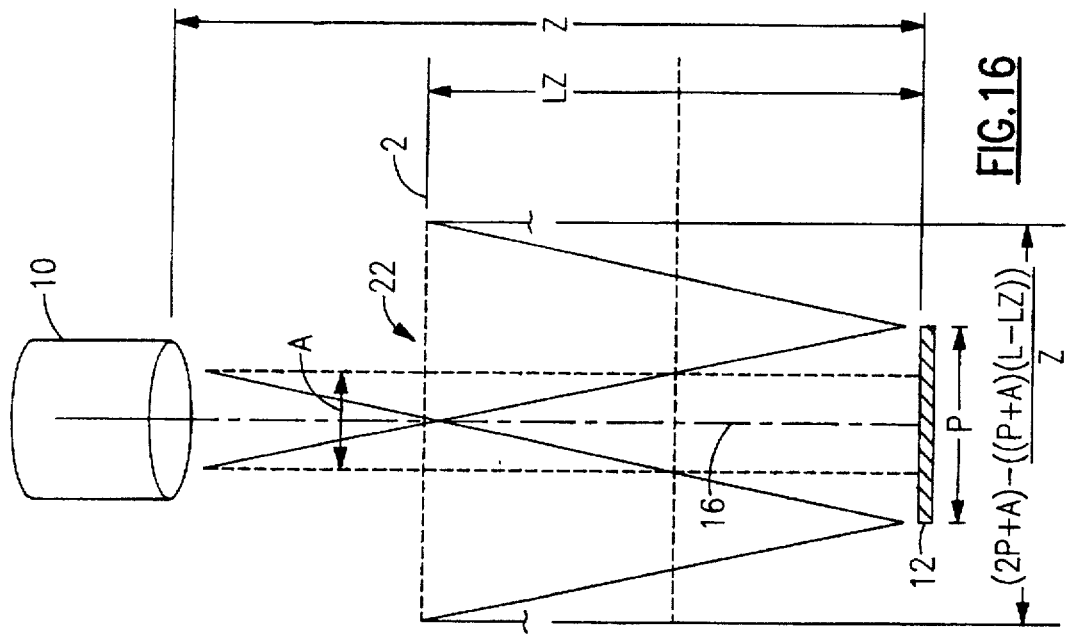
FIG. 16 is a diagrammatic view showing the parameters used to calculate the size of the illumination device.
Figure 15:
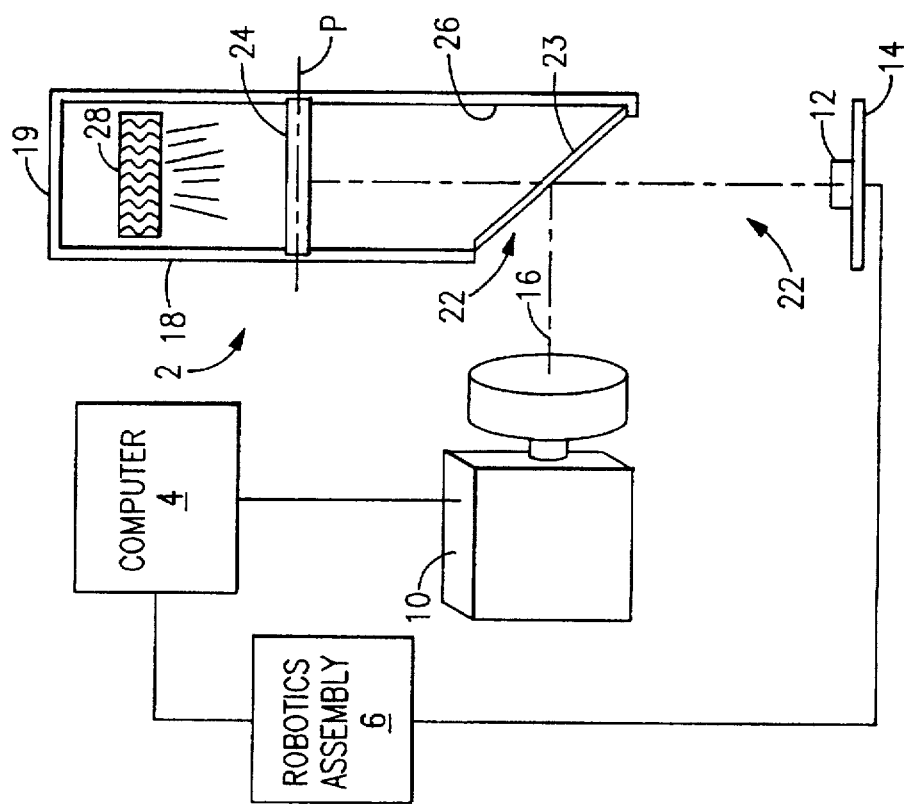
FIG. 15 is a diagrammatic illustration of a still further embodiment of an improved continuous diffuse illumination device, equipped with an inspection camera, in which the entire diffuser is "concealed" from the object being observed by the beam splitter.

As can be seen in FIG. 15, the position of the observation device 10 and the diffuser 24 and the light source 28 are switch. That is, the diffused light will passes directly through the beam splitter 23 and the light reflected by the object 12 is reflected by the beam splitter 23 toward the observation device 10 for viewing. In this embodiment, the location of the light trap 26 is modified and absorbs the diffused light which passes through the beam splitter 23 while the two aperture 22 are located adjacent one another and extend normal to one another. According to this embodiment, the beam splitter 23 completely shields the diffuser 24 from the object 12 For flat planar surfaces (see FIG. 16), the following formula can be used to calculate the proper minimum size of the illumination device.

Minimum Illumination

Device Aperture Size=(2P+A)−((P+A)(Z−LZ)/Z))

Where:

A=the entrance pupil diameter of the lens;
P=the object (field-of-view) width:
Z=the distance between the lens and the object measured along the observation axis; and
LZ=distance from the top of illumination device to the top of object measured along the observation axis. It is to be noted that the first portion of the formula, namely (2P+A), alone describes the proper size of the aperture of the illumination device when the top of the illumination device is located at substantially the same distance from the object 12 to be observed as the camera lens. The second term, namely ((P+A) (Z−LZ) /Z)), specifies that the illumination device becomes smaller in size as the top portion of the illumination device 2 approaches the object 12 to be observed, i.e. the illumination device 2 is located adjacent the object 12 to be observed and remote from the camera lens.

The above formula is very useful for determining an illumination device aperture size for viewing flat reflective planar surfaces. For uneven surfaces, the inventor has not yet derived any precise formula for calculating an optimum illumination geometry. Therefore, a bit of trial and error may be required to find the best solution to achieve for uniform illumination of the object Two useful rules of thumb for use in selecting an aperture size of an illumination device for viewing uneven specular surfaces are to be borne in mind. First, the illumination device should have an aperture which is at least twice the width of the field of view of the object to be observed. Secondly, a bottom portion of the illumination device should be positioned as close to the object to be observed as possible, i.e. adjacent the aperture 22 provided in the base wall 21'. It should also be borne in mind that the further the illumination device is from the object 12 to be observed, the more the illumination device functions like a point light source.

The diffuser 23 may be formed of treated glass, plastic, or some other light translucent material capable of evenly diffusing light cast upon the diffuser by the light source. The interior surface of the housing 18 is painted or coated with a reflective substance which is selected to reflect an amount of light which substantially equal in intensity and character to the light reflected by the beam splitter 23 so as to facilitate uniform illumination of the object to be observed.

Figure 17:
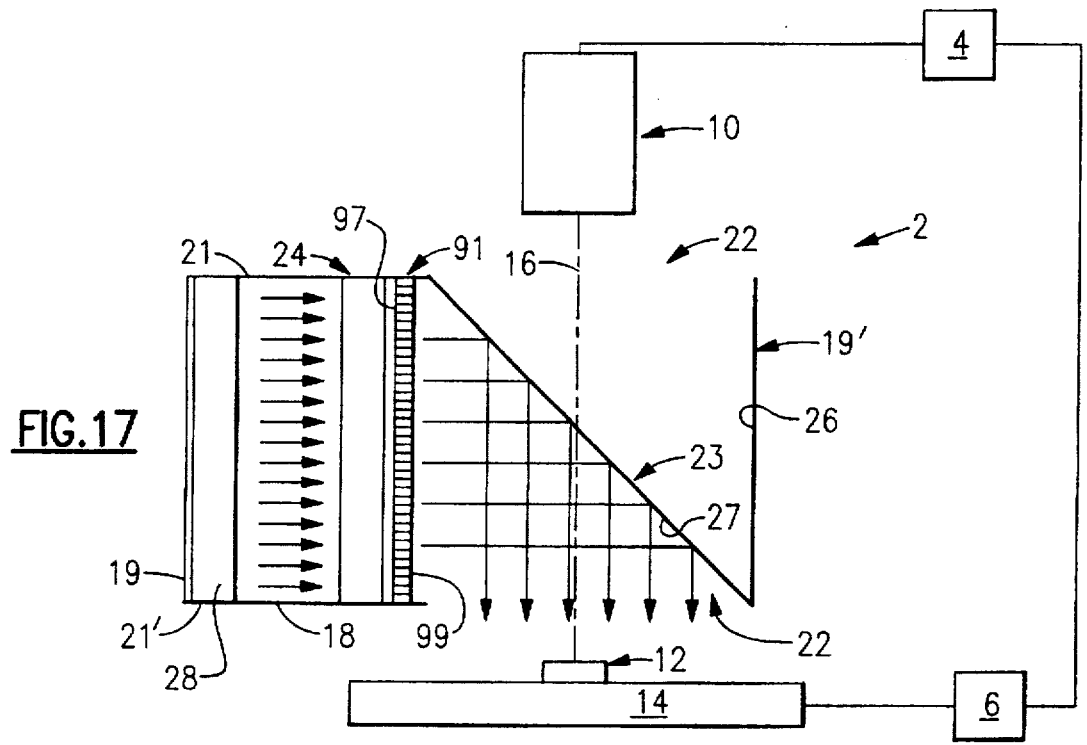
FIG. 17 is a diagrammatic illustration of an improved continuous diffuse illumination device which is equipped with an inspection camera and a microlouver filter.

Turning now to FIG. 17, a brief description of the present invention incorporating a microlouver filter 91 between the diffuser and the beam splitter will now be described. As seen FIG. 17, a housing 18 encases the various components of the continuous diffuse illumination device 2, as with the previously discussed embodiments. The housing 18 includes an aperture 22 formed in both the roof wall 21 and the base wall 21' and the two apertures 22 are spaced from but are concentric with one another and both located along the observation axis 16. The housing 18 accommodates therein: at least one light source 28 adjacent one of the side walls 19, a beam splitter 23 located remote from the light source 28 and positioned along the observation axis 16, a light diffuser located between the light source 28 and the beam splitter 23 and shown generally as element 24, and a light trap 26 supported by the side wall 19' opposite the side wall 19 adjacent the light source 28. In addition, a microlouver filter 91 is positioned between the diffuser 24 and the beam splitter 23. The microlouver filter 91 is immediately adjacent the diffuser 24 and extends parallel to a plane defined by the diffuser 24. The microlouver filter 91 generally has a thickness of from about 0.010 to about 0.060 inches. The microlouver filter is fastened or otherwise secured to an inner surface of the housing 18 in a conventional manner.

Figure 18:
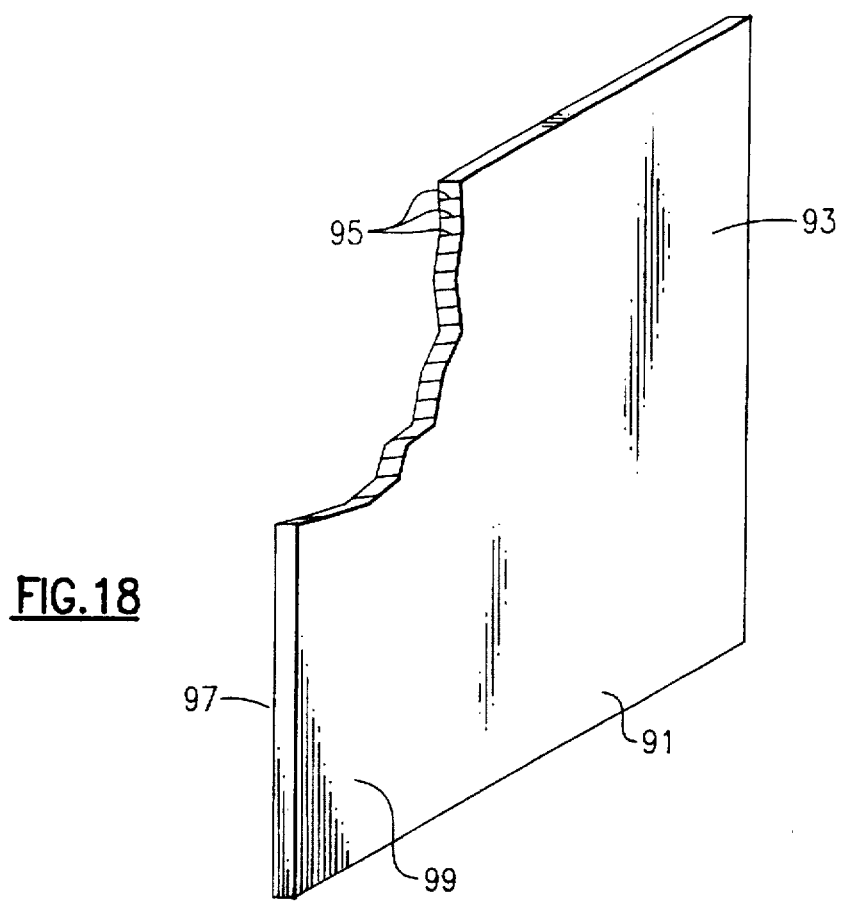
FIG. 18 is a diagrammatic perspective view, shown partly in section, of the microlouver filter of FIG. 17.

The microlouver filter 91 (FIG. 18) comprises a generally high performance plastic film 93 containing a plurality of closely spaced and parallelly arranged microlouvers 95 therein. These microlouvers 95 simulate the characteristics of tiny venetian blinds which block out unwanted ambient light and facilitate control of the illumination direction of the diffused light which is supplied to the beam splitter 23, e.g. the microlouvers 95 of the microlouver filter 91 facilitate the supply of light in a more parallel fashion and prevents light from the diffuser from indirectly illuminating the object 12 to be observed. The microlouvers 95 lie in a plane which forms an angle of about 45° to 90° and preferably about 90° with respect to the light transmission surface 99 of the microlouver filter 91, i.e. they extend perpendicular to the light transmission surface 99. It is to be appreciated that the thickness of the microlouver filter 91 must be sufficient so that the tiny venetian blinds or microlouvers 95 prevent all of the diffused light, diffused by the diffuser 24, from directly illuminating the object 12 to be observed. Accordingly, the spacing of the microlouvers 95 from one another, the angle of microlouvers 95 relative to the light receiving surface 97 and the light transmission surface 99 and the thickness of the microlouver filter 91 have to be taken into consideration, when selecting an appropriate microlouver filter 91, to prevent direct illumination by the diffuser 24 of the object 12 to be observed.

One suitable microlouver filter 91 is a light control film product manufactured by Minnesota Mining and Manufacturing Company of St. Paul, Minn. and sold by their 3M Safety and Security Systems Division under the "3M Light Control Film" brand name. The microlouver filter 91 can be made from polycarbonate or cellulose acetate butyrate and generally has a thickness of about 0.030 inches, or so.

The arrangement of these components is such that the light source 28 casts light upon the diffuser 24 which, in turns, diffuses the light from the light source 28 and casts the diffused light upon the microlouver filter 91 which, in turns, casts the diffused light from the light source 28 upon the beam splitter 23. The beam splitter 23 has a partially reflective first surface 27. A desired portion of the light, e.g. approximately one half of the light from the microlouver filter 91 impacting upon the reflective first surface 27 of the beam splitter 23 is reflected toward the object 12, while the remainder of the light, e.g. approximately one half of the light from the microlouver filter 91, passes through the beam splitter 23 and is absorbed by the light trap 26. Likewise, a portion of the light reflected back by the object 12 is transmitted through the beam splitter 23, along the observation axis 16, toward the camera 10 for viewing while a remainder of the light is reflected back toward the microlouver filter 91. The light returned to the camera 10 is used to determine the precise shape, orientation, and/or other desired feature or characteristic of the object 12 to be observed. As it is well known in this art how to use of the light returned to the camera 10 to determine the shape, orientation, and/or other desired feature or characteristic of the object 12, a detail description concerning the same is not provided herein.

The continuous diffuse illumination device 2 of the invention is particularly suitable for use with a computer controlled robotics assembly or other manufacturing apparatus 6 that utilizes a video camera 10 to image an object 12 on a support table 14 by viewing the object along an observation axis 16 as shown in the FIG. 17. With such an robotics apparatus, electronic signals from the camera 10, resulting from the imaging of the object 12, are used to control the computer 4 which, in turn, controls the operation of the robotics assembly or other manufacturing apparatus 6. The object 12 may be supported on a movable table, conveyor or moveable jig constituting a part of the robotics apparatus permitting the object to be very accurately located with respect to the observation axis 16, the apparatus, or other component(s) with which the object is to be associated.

It is to be appreciated that the angle of the louvers as well as their spacing from one another can be selected such that any light from the filter which directly illuminates the object to be observed can be substantially identical in intensity and in character to the light from the beam splitter.

Since certain changes may be made in the above described illumination device without departing from the spirit and scope of the invention herein involved, it is intended that all matter contained in the above description or shown in the accompanying drawings shall be interpreted merely as examples illustrating the inventive concept herein and shall not be construed as limiting the invention.

What is claimed is:

1. An illumination device for illuminating an object to be observed by a camera along an observation axis extending from the camera to the object, said illumination device comprising:

a housing having at least a first aperture therein alignable with an observation axis;

a partially reflective beam splitter being supported by said housing and being positioned obliquely relative to the observation axis adjacent said at least first aperture;

a light source being arranged to cast light on a first surface of said beam splitter;

a diffuser being positioned between said beam splitter and said light source for diffusing light from said light source as the light passes through said diffuser to said first surface of said beam splitter; and a louver filter being positioned between said beam splitter and said diffuser to prevent direct illumination of an object to be observed by said diffuser whereby said diffuser is only able, during use, to indirectly illuminate a desired portion of the object to be observed, via said louver filter and said beam splitter, when the object is positioned along the observation axis.

2. The illumination device according to claim 1, wherein said louver filter is formed from a plastic film and contains a plurality of closely spaced and parallelly arranged microlouvers members; and the angle and spacing of the microlouver members is selected such that any light from the microlouver filter which directly illuminates the object to be observed is matched to be substantially equal or less than an intensity and in character to light reflected by said beam splitter to the object to be observed.

3. The illumination device according to claim 2, wherein said louver filter has parallel light receiving and light transmission surfaces and said plurality of closely spaced and parallelly arranged microlouvers members extend in planes lying substantially perpendicular to said light receiving and light transmission surfaces.

4. The illumination device according to claim 1, wherein said housing has a second aperture therein which is also alignable with said observation axis and said beam splitter is located between said first aperture and said second aperture.

5. The illumination device according to claim 1, wherein said light source comprises one of a bulb, an incandescent fiber optic, at least one LED, a fluorescent light and an array of lights.

6. The illumination device according to claim 1, wherein said illumination device includes a light trap and said light trap is positioned such that unreflected diffused light, from said light source, which passes through said louver filter and said beam splitter is absorbed by said light trap.

7. The illumination device according to claim 1, wherein the inner surface of the housing is coated with a substance which reflects a sufficient amount of light so as to match a brightness of the diffused light reflected by said beam splitter from said diffuser and said louver filter toward the object to be observed.

8. The illumination device according to claim 1, wherein said illumination device is used in combination with an inspection camera, and said inspection camera is positioned along said observation axis and adjacent a second aperture of said housing to sense light reflected by the object to be observed and passing through said beam splitter.

9. The combination according to claim 8 wherein the combination further includes a computer and assembly equipment, and the computer is connected with said inspection camera and the assembly equipment to control and manipulate the object to be observed, as desired.

10. An inspection system for illuminating an object to be observed by a camera along an observation axis extending from the camera to the object, said inspection system including an illumination device in combination with a camera, said illumination device comprising:

a housing having at least a first aperture therein aligned with an observation axis;

a partially reflective beam splitter being supported by said housing and being positioned obliquely relative to the observation axis adjacent said at least first aperture;

a light source being arranged to cast light on a first surface of said beam splitter;

a diffuser being positioned between said beam splitter and said light source for diffusing light from said light source as the light passes through said diffuser to said first surface of said beam splitter; and a louver filter being positioned between said beam splitter and said diffuser to prevent direct illumination of an object to be observed by said diffuser whereby said diffuser is only able, during use, to indirectly illuminate a desired portion of the object to be observed, via said louver filter and said beam splitter, when the object is positioned along the observation axis defined by the camera thereby facilitating determination by the camera of one of a desired feature and characteristic of the object to be observed.

11. The inspection system according to claim 10, wherein said housing has a second aperture therein also aligned with said observation axis and said beam splitter is located between said first aperture and said second aperture; and said light source comprises one of a bulb, an incandescent fiber optic, at least one LED and a fluorescent light.

12. The inspection system according to claim 10, wherein said louver filter is formed from a plastic film and contains a plurality of closely spaced and parallelly arranged microlouvers members; and said louver filter has parallel light receiving and light transmission surfaces and said plurality of closely spaced and parallelly arranged microlouvers members extend in planes lying substantially perpendicular to said light receiving and light transmission surfaces.

13. The inspection system according to claim 10, wherein said illumination device includes a light trap and said light trap is positioned such that unreflected diffused light, from said light source, which passes through said louver filter and said beam splitter is absorbed by said light trap.

14. The inspection system according to claim 10, wherein the inner surface of the housing is coated with a substance which reflects a sufficient amount of light so as to match a brightness of the diffused light reflected by said beam splitter from said diffuser and said louver filter toward the object to be observed.

15. A method of illuminating an object to be observed by a camera along an observation axis extending from the camera to the object, said method comprising the steps of:

utilizing a housing having two aligned apertures therein which are both aligned with an observation axis;

supporting a partially reflective beam splitter within said housing between said apertures and along the observation axis;

arranging a light source to cast light on a first surface of said beam splitter;

positioning a diffuser between said beam splitter and said light source for diffusing light from said light source as the light passes through said diffuser toward said beam splitter;

positioning a louver filter between said beam splitter and said diffuser to prevent direct illumination an object to be observed by said diffuser;

supplying light, from said light source, through said diffuser and said louver filter;

reflecting a portion of said light, via said beam splitter, toward the object to be observed;

allowing a portion of light reflected back by said object to be observed to pass through said beam splitter and be sensed by said camera whereby said diffuser is only able, during use, to indirectly illuminate a desired portion of the object to be observed when the object is positioned along the observation axis.

16. The method according to claim 15, further comprising the steps of forming said louver filter from a plastic film and providing a plurality of closely spaced and parallelly arranged microlouvers members within said plastic film.

17. The method according to claim 15, further comprising the step of providing said louver filter with parallel light receiving and light transmission surfaces and arranging said plurality of closely spaced microlouvers members parallel to one another and extending in planes lying substantially perpendicular to said light receiving and light transmission surfaces.

18. The method according to claim 15, further comprising the step of utilizing one of a bulb, an incandescent fiber optic, at least one LED and a fluorescent light as said light source.

19. The method according to claim 15, further comprising the steps of providing a light trap and positioning said light trap such that unreflected diffuse light which passes through said beam splitter is absorbed by said light trap.

20. The method according to claim 15, further comprising the steps of coating an inner surface of the housing with a substance which reflects a sufficient amount of light so as to match a brightness of the diffused light reflected by said beam splitter from said diffuser and said louver filter toward the object to be observed.

* * * * *